United States Patent [19]
Jackson et al.

[11] Patent Number: 5,702,388
[45] Date of Patent: Dec. 30, 1997

[54] ORTHOPAEDIC RETAINER ATTACHABLE TO AN ELONGATE MEMBER

[75] Inventors: Kenneth S. Jackson, Warsaw; Charles D. Persons, Columbia City; Robert D. Krebs, Warsaw; Gregory G. Price, Warsaw; Joel P. Bales, Warsaw, all of Ind.

[73] Assignee: Zimmer, Inc., Warsaw, Ind.

[21] Appl. No.: 603,818

[22] Filed: Feb. 20, 1996

[51] Int. Cl.$^6$ .................................................. A61B 17/56
[52] U.S. Cl. .......................... 606/54; 606/151; 24/115 G; 24/136 R
[58] Field of Search .................. 602/79; 606/53–59, 606/151; 24/4, 6, 3.11, 326, 351, 457, 460, 462, 115 G, 136 R

[56] References Cited

U.S. PATENT DOCUMENTS

| | | | |
|---|---|---|---|
| D. 264,662 | 6/1982 | Bisk et al. | D6/257 |
| D. 291,247 | 8/1987 | Weilbacher | D24/27 |
| 4,328,605 | 5/1982 | Hutchison et al. | 24/115 G |
| 4,335,838 | 6/1982 | Bisk et al. | 223/91 |
| 4,356,600 | 11/1982 | Welch | 24/30.5 R |
| 4,394,791 | 7/1983 | Groth | 24/30.5 R |
| 4,943,293 | 7/1990 | Lee, Jr. | 606/96 |
| 5,281,221 | 1/1994 | Tadych | 606/53 |
| 5,305,499 | 4/1994 | Oeticker | 24/20 |
| 5,305,500 | 4/1994 | Tucker | 24/30.5 R |
| 5,360,020 | 11/1994 | Lee, Sr. et al. | |
| 5,447,492 | 9/1995 | Cartmell et al. | 602/58 |

OTHER PUBLICATIONS

Cole–Parmer Instrument Company—Tubing Accessories—pp. 1571,1572—No date available.
Thomas Scientific—Clamps—p. 333—No date available.
Duraflex—Posi Grip Cord Grip—No date available.
Zimmer, Inc.—Brochure—Torus External Fixation System—c1994.

*Primary Examiner*—Michael Buiz
*Assistant Examiner*—Daphna Shai
*Attorney, Agent, or Firm*—Margaret L. Geringer

[57] ABSTRACT

The invention is directed to a retainer (10, 12, 70) for securing a sponge (16) at the point of entry for an orthopaedic elongate member (14). The retainer (10, 12, 70) is removably attachable to the elongate member (14) adjacent the sponge. The retainer, in one embodiment, includes a body (22) having a bottom (24) and a side (26), with the side (26) being disposed adjacent to the bottom (24). The body (22) further includes an opening (34) associated with each of the bottom (24) and the side (26). The opening (34) is configured for receiving the elongate member (14) therein. A clamp (40) is movably attached to the body (22) and engageable with the elongate member (14) for retaining the elongate member (14) within the opening (34). A resilient member (50) is integral or engaged with the clamp (40) for biasing the clamp (40) into engagement with the elongate member (14).

25 Claims, 2 Drawing Sheets

5,702,388

ORTHOPAEDIC RETAINER ATTACHABLE TO AN ELONGATE MEMBER

BACKGROUND OF THE INVENTION

1. Field of the Invention

The present invention relates to orthopaedic external fixation apparatus, and, more particularly, relates to a retainer for securing a wound site dressing at the point of entry for an orthopaedic elongate member.

2. Description of the Related Art

Fixation of broken bones may require the use of orthopaedic elongate members, such as pins, screws or the like, which are inserted into the injured limb, with an end protruding outwardly through the patient's skin. Such elongate members may be components of external fixation systems and may remain in position for several days, weeks or even months depending upon the severity of the injury and other factors. In order to minimize the risk of infection, a wound site dressing, such as an absorbent sponge or other suitable dressing, may be regularly applied to the point of entry of each elongate member through the patient's skin. An antiseptic could be added or included in the dressing, if desired.

A retainer may be attached to the elongate member and disposed against the sponge to maintain the sponge against the patient's skin. For example, it is known to use a flat disk with a centered hole and slot radially extending from the hole to the periphery of the disk to fit over the pin and press against a slotted sponge which is also fitted over the pin. However, typically, different sizes of disks are needed to accommodate different diameter pins. In addition, U.S. Pat. No. 4,943,293 (Lee, Jr.) discloses a surgical pin site shield having a radially extending slot therein. A radially extending opening in the collar threadingly engages a thumb screw which may be rotated into the collar and the slot. The thumb screw engages the elongate member to maintain the elongate member within the radially extending slot. The pin site shield retainer as disclosed by U.S. Pat. No. 4,943,293 requires a two-handed operation to attach the collar to the elongate member. The collar must be held about the elongate member with one hand while the thumb screw is tightened with the other hand. An example of another pin site shield retainer is disclosed by U.S. Pat. No. 5,360,020 (Lee, Sr., et al.).

What is needed in the art is a retainer for a surgical sponge which may be relatively easily and quickly connected to an elongate member.

What is further needed in the art is a retainer for a surgical sponge which accommodates various positions of the retainer relative to the skin of the patient.

SUMMARY OF THE INVENTION

The present invention provides a retainer which is attachable to an orthopaedic elongate member, such as a pin or wire, wherein the retainer provides faster and easier attachment to the elongate member through the use of side loading in a side opening.

The invention comprises, in one form thereof, a retainer for securing a wound site dressing, such as a sponge, at the point of entry for an orthopaedic elongate member. The retainer is removably attachable to the elongate member adjacent the sponge. The retainer includes a body having a bottom and a side, with the side being disposed adjacent to the bottom and the bottom to be positioned against or generally facing toward the sponge. The body further includes an opening associated with each of the bottom and the side. The opening is configured for receiving the elongate member therein. A clamp is movably attached to the body and engageable with the elongate member for retaining the elongate member within the opening. A resilient member is engaged with or integrally formed with the clamp for biasing the clamp into engagement with the elongate member.

An advantage of the present invention is that the elongate member may be securely loaded faster and more easily into and attached to the retainer, and, as such, the retainer facilitates applying and changing the sponge dressing.

Another advantage is that the elongate member may be loaded into the retainer at or near a desired point of attachment, as opposed to sliding the retainer over the elongate member.

A further advantage is that the retainer of the present invention can accommodate elongate members of various diameters.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate one preferred embodiment of the invention, in one form, and such exemplifications are not to be construed as limiting the scope of the invention in any manner.

DETAILED DESCRIPTION OF THE INVENTION

Figure 1:
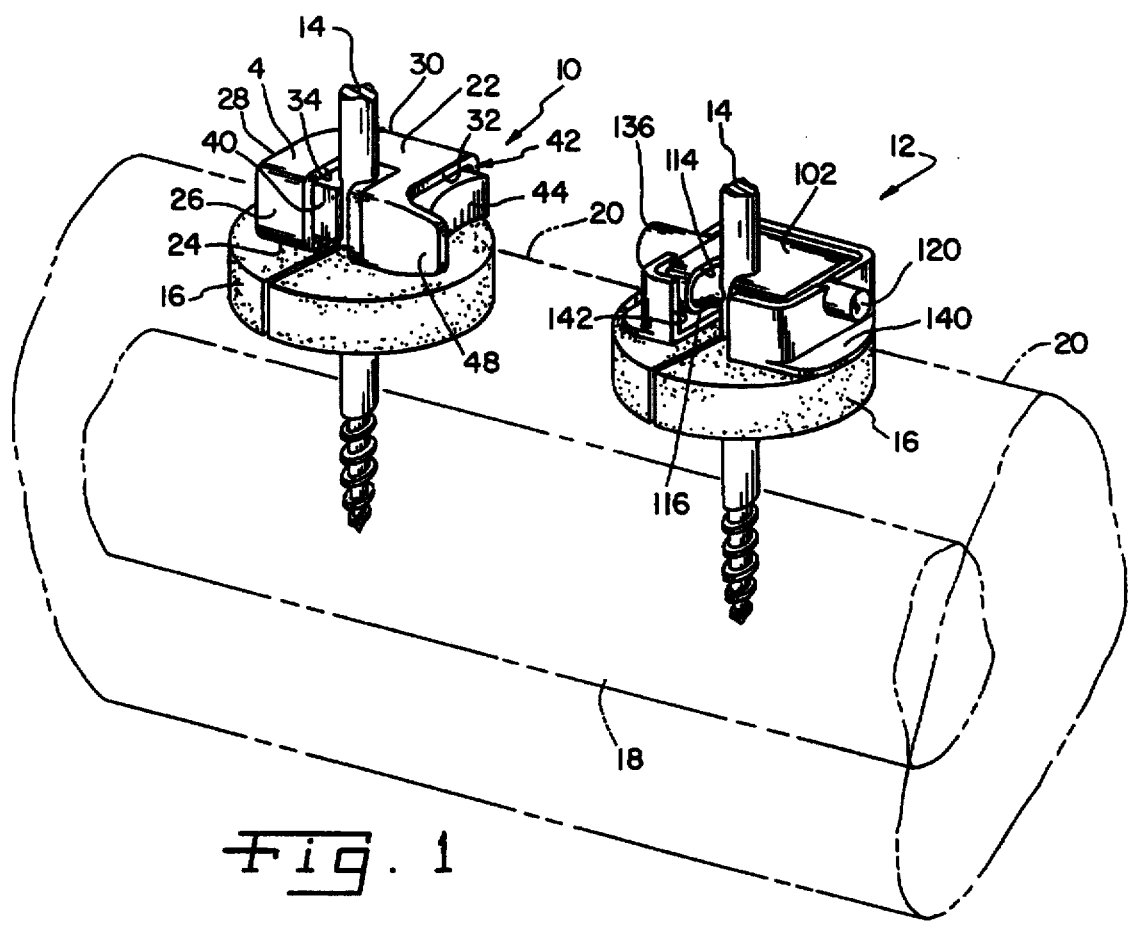
FIG. 1 is a perspective view of two embodiments of the sponge retainer of the present invention, when attached to an external fixator bone pin.

Referring now to the drawings and particularly to FIG. 1, there is shown a perspective view of two embodiments of retainers 10, 12 which are attached to elongate members 14 and disposed adjacent to surgical sponges 16. Elongate members 14 may be in the form of a pin, rod, wire, screw, nail or other orthopaedic member. Elongate members 14 are attached to a bone (shown in phantom lines and referenced as 18) and protrude through the skin of a patient (shown in phantom lines and referenced as 20). Retainers 10, 12 assist in maintaining antiseptic sponges 16 against skin 20 at the point of entry through the skin (not shown).

Figure 2:
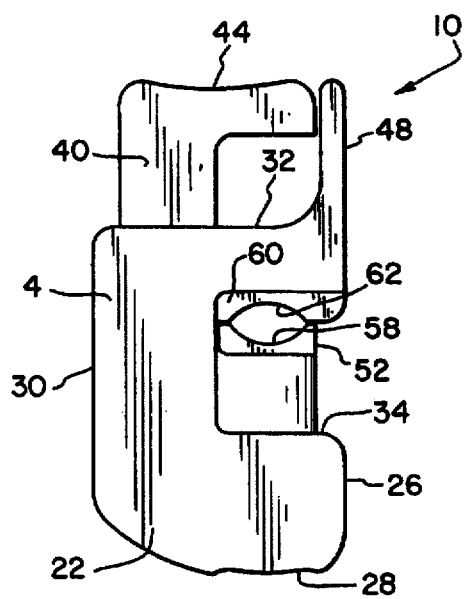
FIG. 2 is a top view of the sponge retainer shown on the left in FIG. 1.
Figure 3:
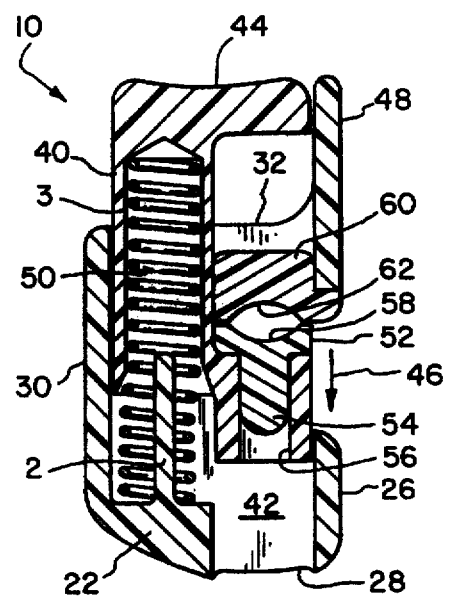
FIG. 3 is sectional, top view of the sponge retainer shown in FIG. 2.

Referring now to FIGS. 1–3, conjunctively, retainer 10 will be described in greater detail. Retainer 10 includes a body 22 having a bottom 24, which is positioned against slotted sponge 16 in FIG. 1, and sides 26, 28, 30 and 32. Each side 26, 28, 30 and 32 is disposed adjacent to bottom 24. Body 10 further includes an opening 34 associated with bottom 24 and side 26. Opening 34 is configured for receiving elongate member 14 therein. Top 4 of body 22 is oppositely located from bottom 24 with side 26 therebetween. Opening 34 extends through side 26 and bottom 24 and top 4 for receiving the elongate member 14 therein.

Retainer 10 also includes a clamp 40 which is slidably disposed within an aperture 42 formed in body 22. Clamp 40 is thus interconnected to and slidably disposed within body 22. Clamp 40 includes a thumb lever 44 which may be depressed by a user such that clamp 40 slides in the direction indicated by directional arrow 46 (FIG. 3). A stabilizer flange 48 extending from body 22 is disposed adjacent to thumb lever 44 and inhibits tipping of clamp 40 relative to body 22. As will be appreciated, the extent of sliding movement of clamp 40 relative to body 22 is limited by the interference between clamp 40 and body 22 when thumb lever 44 is depressed and clamp 40 bottoms out within body 22. It is noted that the thumb lever 44 and side 28 (i.e. the gripping surfaces used for depressing clamp 40) may be textured, if desired, to enhance gripping retainer 10.

Clamp 40 may include a jaw 52 which is attached thereto. In the embodiment shown in FIG. 3, jaw 52 includes a projection 54 which extends into a recess 56 of clamp 40. Jaw 52 includes a curved surface 58 in the form of a concave surface which assists in maintaining elongate member 14 within retainer 10.

A reactionary jaw 60 is attached to body 22 and is engageable with elongate member 14. Reactionary jaw 60 may include a curved surface 62, similar to curved surface 58, which is engageable with elongate member 14.

A resilient member 50 which, in the embodiment shown in FIG. 3, is in the form of a compression spring, is engaged at opposing ends thereof with each of body 22 and clamp 40. Spring 50 biases clamp 40 into engagement with elongate member 14. In the embodiment shown in FIGS. 2 and 3, resilient member 50 and clamp 40 together define a clamp assembly. The spring 50 is held in spring chamber 3 of clamp 40 and is positioned over post 2 of body 22, although any suitable manner of operatively providing spring 50 between clamp 40 and body 22 may be utilized.

It is noted that clamp 40 and spring 50 can conveniently be inserted into body 22 prior to attaching jaw 60 to body 22. Then jaw 60 can be attached to body 22 which retains the clamp 40 and spring 50 within body 22.

Figure 4:
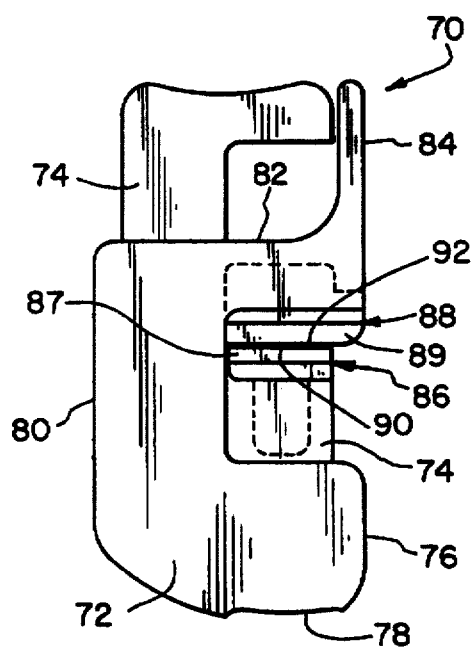
FIG. 4 is a top view of another embodiment of the sponge retainer of the present invention which is similar to FIGS. 2 and 3, but with flat jaws.

Referring now to FIG. 4, another embodiment of a retainer 70 of the present invention is shown. Retainer 70 includes a body 72 and clamp 74 which are very similar to body 22 and clamp 40 shown in FIGS. 2 and 3. For example, body 72 includes sides 76, 78, 80 and 82 which correspond to sides 26, 28, 30 and 32 shown in FIGS. 2 and 3. Moreover, body 72 includes a stabilizer flange 84 which is similar to stabilizer flange 48 shown in FIGS. 2 and 3. However, in contrast with retainer 10, retainer 70 includes a jaw 86 and reactionary jaw 88 which each have a flat surface or flat face 90, 92, respectively, which are engageable with elongate member 14. The faces 90, 92 of jaws 86, 88 may be separately formed pads 87, 89 which are bonded or otherwise attached to jaws 86, 88. This enables the separate pads to be formed of a more resilient material for better gripping. The flat faces 90, 92 readily accommodate a variety of pin diameters or shapes. Similar to retainer 10 shown in FIGS. 2 and 3, jaw 86 and reactionary jaw 88 are respectively attached to clamp 74 and body 72.

It is noted that jaws 86, 88 may have flat faces 90, 92, as shown. Alternatively, faces 90, 92 may be concave (as with the jaws 60 and 54 of the embodiment of FIG. 3) or convex (not shown). These faces 90, 92 generally may be contoured in any suitable manner to provide effective clamping on a wide range of sizes and shapes of pins. In addition, these faces 90, 92 may be smooth or textured, as desired, to enhance clamping ability. It is noted that separate pads 87, 89 may be rigidly attached to jaws 86, 88 or rotatively attached, such as by a ball swivel connection (not shown). Such swivel connection provides for angulation or flexibility for attaching the retainer to the pin 14. These variations may be incorporated on any suitable embodiment of this invention, as desired.

Figure 5:
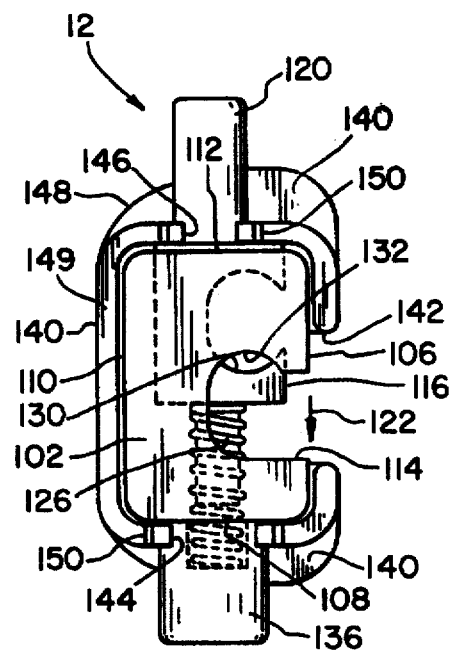
FIG. 5 is a top view of the sponge retainer shown on the right in FIG. 1.
Figure 6:
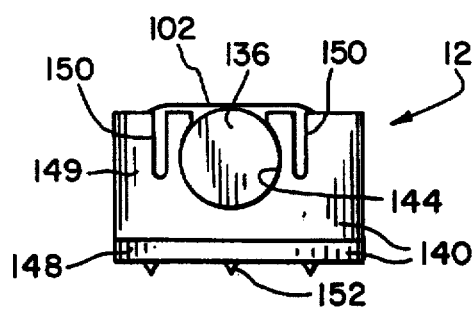
FIG. 6 is an end view of the sponge retainer shown in FIG. 5.

Referring now to FIGS. 5 and 6, retainer 12 shown in FIG. 1 will be described in greater detail. Retainer 12 includes a body 102 having a bottom (not numbered) and sides 106, 108, 110 and 112. Each side 106, 108, 110 and 112 is disposed adjacent to the bottom. Body 102 further includes an opening 114 associated with the bottom and side 106. Opening 114 is configured for receiving elongate member 14 (FIG. 1) therein.

Retainer 12 also includes a clamp 116 which is slidably disposed within an aperture (not numbered) formed in body 102 (similar to aperture 42 formed in body 22 of retainer 10). Clamp 116 is thus interconnected with and slidably disposed within body 102. Clamp 116 includes a projection 120 which may be depressed by a user such that clamp 116 slides in the direction indicated by directional arrow 122. As will be appreciated, the extent of sliding movement of clamp 116 relative to body 102 is limited by the interference between clamp 116 and body 102 when projection 120 is depressed and clamp 116 bottoms out within body 102.

Body 102 includes a projection 136 which extends therefrom and is disposed generally opposite from projection 120. Projections 120, 136 allow retainer to be grasped, e.g., between a thumb and index finger of a user, for depressing projection 120 and thereby moving clamp 116 in the direction indicated by arrow 122.

According to another aspect of the invention, retainer 12 may include a foot 140 which is pivotally connected to body 102 and disposed adjacent to the bottom (not shown) of body 102. More particularly, foot 140 includes a bottom platform 148 and a containing wall 149 extending therefrom. Wall 149 includes arcuate openings 144, 146 which extend about respective cylindrical projections 136, 120 and pivotally connect foot 140 to body 102 and clamp 116. Wall 149 may also include slots 150 to provide a simple snap fit assembly of projections 136, 120 to foot 140. This also enables the foot 140 to be optionally removable. It is noted that in the embodiment of FIGS. 5 and 6, the wall 149 holds clamp 116 and body 102 together. However, the clamp 116 and body 102 could be designed to be held together when not contained in foot 140, if desired. This would enable retainer 12 to be used with or without foot 140. Foot 140 includes an opening 142 which is aligned with body opening 114 and which is configured for receiving elongate member 14 therethrough. Platform 148 of foot 140 is adapted for engagement with sponge 16 and accommodates various orientations or positions of retainer 12 relative to skin 20 of the patient. That is, elongate member 14 may extend outwardly through the skin at other than a right angle and sponge 16 is still retained against skin 20 using foot 140. The foot 140 provides more uniform pressure across sponge 16 regardless of the angle of the pin or elongate member 14 to the skin interface. The foot 140 may pivot about body 102 and clamp 116, but the body is preferably constrained axially and laterally within the wall 149 of foot 140. Foot 140 may include gripping projections 152 on platform 148 to engage sponge 16. Such gripping projections could also be used on the bottom 24 (not shown) on the embodiment of FIG. 3, if desired.

Clamp 116 may include an integrally formed jaw or a curved surface 130 in the form of a concave surface which assists in maintaining elongate member 14 within retainer 12. Likewise, body 102 may include an integrally formed jaw or a curved surface 132, similar and opposite to curved surface 130, which is engageable with elongate member 14. However, the jaw surfaces 130, 132 may be flat (not shown) or otherwise contoured, as desired.

A resilient member 126 which, in the embodiment shown, is in the form of a compression spring (FIG. 5) is engaged at opposing ends thereof with each of body 102 and clamp 116. Spring 126 biases clamp 116 into engagement with elongate member 14. In the embodiment shown in FIGS. 5 and 6, resilient member 126 and clamp 116 together define a clamp assembly.

It is noted that the retainer components, including the body, the clamp and the foot, may be molded of plastic, although any suitable materials and manufacturing methods may be utilized, as desired. The resilient member may be a separate spring, and may be made of metal or any other suitable material. Alternatively, the resilient member may be integrally molded with either the body or the clamp, if desired. The jaws 52 and 60 may also be molded of plastic, such as PVC, or the jaws or jaw pads 87, 89 may be a more resilient material, such as silicone, for enhanced gripping of elongate member 14. However, once again, any suitable materials may be utilized.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A retainer for securing a wound site dressing at the point of entry for an orthopaedic elongate member, said retainer being removably attachable to the elongate member adjacent the dressing said retainer comprising:
   a body including a bottom and a side, said side disposed adjacent said bottom, and wherein said body further includes a top oppositely located from said bottom with said side positioned therebetween, said body further including an opening extending through said side and said bottom and said top, said opening configured for receiving the elongate member therein, whereby the elongate member is able to be received laterally in a side loading manner through said opening in the side, top, and bottom of said body;
   a clamp movably attached to the body and engageable with the elongate member for retaining the elongate member within said opening; and
   a resilient member for biasing said clamp into engagement with the elongate member.

2. The retainer of claim 1, wherein said resilient member comprises a spring engaged with each of said clamp and said body.

3. The retainer of claim 2, wherein said spring comprises a compression spring.

4. The retainer of claim 1, wherein said body includes an aperture, and wherein said clamp is slidably disposed within said aperture.

5. The retainer of claim 4, wherein said resilient member is engaged with each of said body and said clamp for biasing said clamp into engagement with the elongate member.

6. The retainer of claim 1, wherein said clamp comprises a jaw which is engageable with the elongate member.

7. The retainer of claim 6, wherein said clamp jaw includes a curved surface engageable with the elongate member.

8. The retainer of claim 6, wherein said clamp jaw includes a flat surface emgageable with the elongate member.

9. The retainer of claim 1, wherein said body further comprises a reactionary jaw engageable with the elongate member.

10. The retainer of claim 9, wherein said reactionary jaw includes a curved surface engageable with the elongate member.

11. The retainer of claim 1, wherein the elongate member comprises one of a pin, rod, wire, screw and nail.

12. The retainer of claim 1, wherein said clamp extends from a first end of said body, and wherein said body further includes a stabilizer flange extending from said first end, said stabilizer flange engageable with said clamp for inhibiting tipping of said clamp relative to said body.

13. A retainer for securing a wound site dressing at the point of entry for an orthopaedic elongate member, said retainer being removably attachable to the elongate member adjacent the dressing, said retainer comprising:
   a body including a bottom and a side, said side disposed adjacent said bottom, and wherein said body further includes a top oppositely located from said bottom with said side positioned therebetween, said body further including an opening extending through said side and said bottom and said top, said opening configured for receiving the elongate member therein, whereby the elongate member is able to be received laterally in a side loading manner through said opening in the side, top, and bottom of said body; and
   a clamp assembly movably attached to the body, said clamp assembly including a clamp which is engageable with the elongate member for retaining the elongate member within said opening, said clamp assembly further including a resilient member engaged with said clamp for biasing said clamp toward the elongate member.

14. The retainer of claim 13, wherein said resilient member comprises a spring engaged with each of said clamp and said body.

15. The retainer of claim 14, wherein said spring comprises a compression spring.

16. The retainer of claim 13, wherein said body includes an aperture, and wherein said clamp is slidably disposed within said aperture.

17. The retainer of claim 16, wherein said resilient member is engaged with each of said body and said clamp, said resilient member biasing said clamp into engagement with the elongate member.

18. The retainer of claim 13, wherein said resilient member and said clamp are separate from and engaged with each other.

19. A retainer for securing a wound site dressing at the point of entry for an orthopaedic elongate member, said retainer being removably attachable to the elongate member adjacent the dressing, said retainer comprising:

a body including a bottom, said body further including an opening associated with said bottom, said opening configured for receiving the elongate member therein; and a foot pivotally connected to said body and disposed adjacent to said bottom, said foot including an opening configured for receiving the elongate member therein, said foot adapted for engagement with the dressing.

20. The retainer of claim 19, wherein said body includes a pair of projections extending therefrom, and wherein said foot is pivotally connected to said projections.

21. The retainer of claim 19, wherein said body includes a side disposed adjacent to said bottom, and wherein said opening is associated with each of said bottom and said side.

22. The retainer of claim 19, further comprising a clamp movably attached to the body and engageable with the elongate member for retaining the elongate member within said opening.

23. The retainer of claim 19, wherein each of said body and said clamp include a projection extending therefrom, and wherein said foot is pivotally connected to said projections.

24. The retainer of claim 19, wherein the foot includes a bottom platform adjacent said bottom of said body and a containing wall extending from the platform to support the body therein.

25. The retainer of claim 19, wherein the opening in said foot is aligned with the opening in said body for receiving the elongate member therein.

* * * * *